United States Patent [19]

Urushida

[11] 4,237,925
[45] Dec. 9, 1980

[54] ANESTHESIA APPARATUS

[75] Inventor: Yoshihisa Urushida, Kodaira, Japan

[73] Assignee: Citizen Watch Co., Ltd., Tokyo, Japan

[21] Appl. No.: 869,183

[22] Filed: Jan. 12, 1978

[30] Foreign Application Priority Data

Jan. 18, 1977 [JP] Japan .................................. 52/4247
Oct. 7, 1977 [JP] Japan .................................. 52/120607

[51] Int. Cl.³ ...................... A61M 17/00; F16K 19/00
[52] U.S. Cl. ............................. 137/552; 128/203.25; 137/607; 137/636.1; 137/637; 251/205
[58] Field of Search ............ 137/595, 607, 636, 636.1, 137/637, 865, 866, 552; 222/134; 128/203.25

[56] References Cited

U.S. PATENT DOCUMENTS

| 1,793,608 | 2/1931 | Gramberg | 137/607 |
| 2,040,663 | 5/1936 | Mallet et al. | 137/636.1 |
| 2,171,992 | 9/1939 | Rantine | 137/636 X |
| 3,139,262 | 6/1964 | Morris et al. | 251/205 |
| 3,739,799 | 6/1973 | Bickford et al. | 137/100 X |
| 3,875,968 | 4/1975 | Olofsson et al. | 137/636.1 |
| 3,905,363 | 9/1975 | Dudley | 128/145.8 |

Primary Examiner—Martin P. Schwadron
Assistant Examiner—Richard Gerard

Attorney, Agent, or Firm—Jordan and Hamburg

[57] ABSTRACT

An anesthesia apparatus which comprises at least two flow meters, an oxygen gas supply means for supplying oxygen gas to one of said flow meters, a nitrous oxide gas supply means for supplying nitrous oxide gas to another one of said flow meters, at least two flow rate adjustment valves disposed between the one of said flow meters and said oxygen gas supply means and between said another one of said flow meters and said nitrous oxide gas supply means, respectively, each of said flow rate adjustment valve including a valve element having a predetermined shape to vary the rate of flow of each of said gases substantially in proportion to the amount of movement of said valve element, a flow control means connected to said flow rate adjustment valves for actuating said valves, and a flow rate adjustment means operatively connected to said flow control means and operative to set a selected angular position of said flow control means with respect to said flow rate adjustment valves for thereby determining the relative proportions of said gases, said flow control means being operative to move said flow rate adjustment valves while maintaining said selected angular position for thereby varying the total rate of flow of said gases substantially without varying the relative proportions thereof.

23 Claims, 10 Drawing Figures

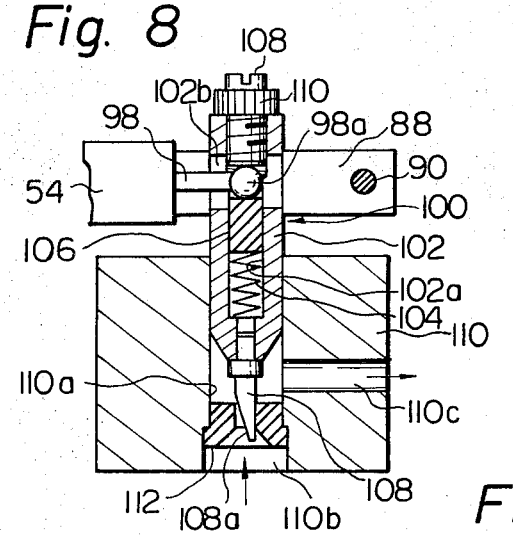
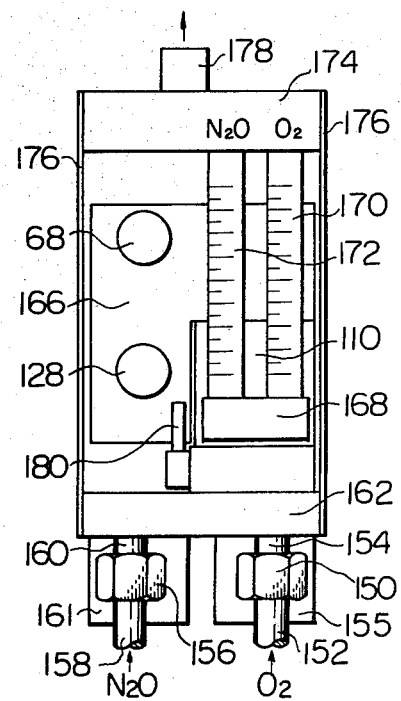
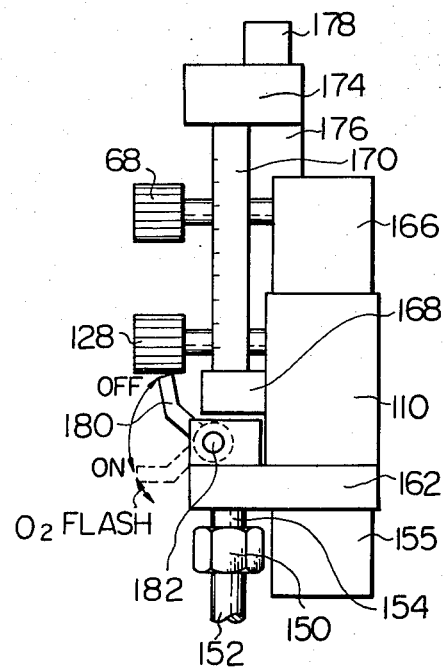

ANESTHESIA APPARATUS

This invention relates to a control device for controlling the flow rate of a fluid, and more particularly to a device for controlling the flow rate and mixing proportions of a gas in continuous flow anesthesia apparatus.

Anesthesia apparatus which is now in widest use is of the continuous flow-type. In most of this apparatus, a single flow rate adjustment valve and flowmeter are provided for each gas. Thus, in order to utilize a large variety of gases, a flow rate adjustment valve and flowmeter must be provided for each individual gas. When mixing a plurality of gases, individual flow rates are determined by manipulation of the valves while observing the flow rate readings on respective flowmeters. After the flow rates are decided, the mixing proportions and total flow rate are obtained by computations based upon the individual gas flow rates.

Anesthesia apparatus normally utilizes a mixture of the two gases oxygen and nitrous oxide. However, very few types of anesthesia apparatus are known which allow the total gas flow rate to be regulated with just one adjustment knob while holding the mixing proportions of the two gases constant, or which allow the mixing proportions to be varied with one adjustment knob while holding the total gas flow rate constant.

In terms of superior operability, anesthesia apparatus capable of adjusting the individual flow rates of two gases without affecting the mixing proportions of the gases, and further capable of freely varying the mixing proportions while maintaining the total flow rate of gas constant, namely anesthesia apparatus which allows independent variation of the total gas flow rate and the mixing proportions, is preferred over the conventional anesthesia apparatus in which the flow rates of the mixing gases must be individually regulated. Even the sole apparatus which possesses this superlative operability, as disclosed in U.S. Pat. No. 3,739,799 and now being marketed, presents a critical drawback. Namely, a mixture control dial includes graduations which are unequally spaced, and when increasing the flow rate there is no uniformity between flow rate variation and the rotation of a regulating knob. For large and small flow rates there is thus an exceedingly large difference in the amount of flow rate variation for each revolution of the regulating knob.

It is, therefore, an object of the present invention to provide an anesthesia apparatus which can overcome the shortcomings encountered in the prior art.

It is another object of the invention to provide an anesthesia apparatus which has an extremely simple structure.

It is still another object of the present invention to provide an anesthesia apparatus in which the degree of adjustment member control is proportional to flow rate and the proportions of the mixing fluids.

These and other objects, features and advantages of the present invention will become more apparent from the following description when taken in conjunction with the accompanying drawings, in which:

FIG. 8 is a cross sectional view of a flow rate adjustment valve and associated parts shown in FIG. 7;

FIG. 9 is a front view of the anesthesia apparatus shown in FIG. 7; and

FIG. 10 is a side view of the anesthesia apparatus shown in FIG. 9.

Figure 1:
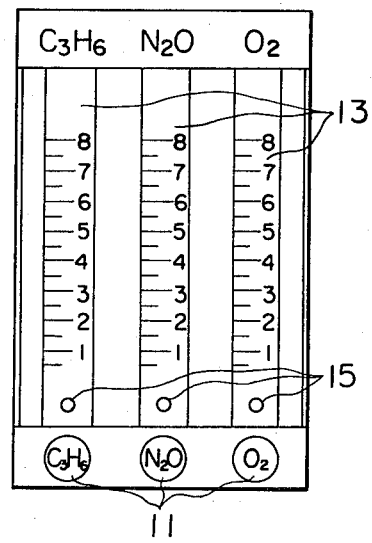
FIG. 1 is a schematic view of an example of a conventional anesthesia apparatus.

FIG. 1 illustrates a conventional anesthesia apparatus. Flow rate adjustment knobs are designated at 11. Flow-meters 13 provide an indication of flow rate (number of liters per minute) as indicated by the position of a float 15 within a tube. In apparatus of this type, the flow rate and the proportions of two mixing gases are set to desired values by regulating the flow rate adjustment valves 11. The result of the adjustments is read off the flow meters which are linked to the adjustment valves, so that it is necessary to perform computations to determine the respective ratios of total flow rate and the flow rate desired of each gaseous component. In consequence, it is almost impossible to vary the relative proportions of the two gaseous components without affecting the total flow rate, or to smoothly vary the total flow rate without affecting the proportions of the gas mixture.

In accordance with the present invention, continuous variation of the oxygen and nitrous oxide proportions of a gaseous mixture while holding total flow rate constant, and continuous variation of the total flow rate without affecting the proportions of the gas mixture can be accomplished by means of the following structure.

A flow rate adjustment valve is provided with the capability of varying flow rate in proportion to its degree of adjustment. This may be achieved by establishing a proportional relation between the angle through which an adjustment knob is turned and the opening area of a flow rate adjustment valve as defined by an orifice and a needle valve which determines the flow rate. In actual practice, a flow rate adjustment valve comprises a cylindrical valve member in intimate contact with a bore of a valve body, the end of the valve member being cut off at an oblique angle. In such a case the opening area of the adjustment valve is a sectional area lying in a plane perpendicular to the axis of the valve and passing through a point spaced a given distance along the axis of the valve from the starting point of the cut. If the valve member is cut such that the value of the sectional area is proportional to the distance from the starting point of the cut (i.e., where the sectional area is zero), the flow rate can be made proportional to the amount of movement of the valve member through the orifice.

Figure 2:
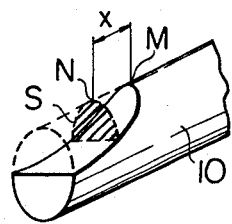
FIG. 2 is a fragmentary perspective view illustrating a principle of a cylindrical needle valve for a flow rate adjustment valve to be incorporated in an anesthesia apparatus according to the present invention.

FIG. 2 shows an example of a cylindrical needle valve 10 for a flow rate adjustment valve in which the tip of the needle valve is cut off at an oblique angle. In this case, let S represent the sectional area of the removed portion of the needle valve, i.e., a sectional area lying in a plane perpendicular to the axis of the valve and passing through a point N spaced a distance x along the axis of the valve from the starting point M of the cut. If the shape of the removed valve portion is determined so as to satisfy the relation $s=kx$, the degree of movement of the needle valve 10 can be made proportional to the amount of gas passing therethrough.

Figure 3:
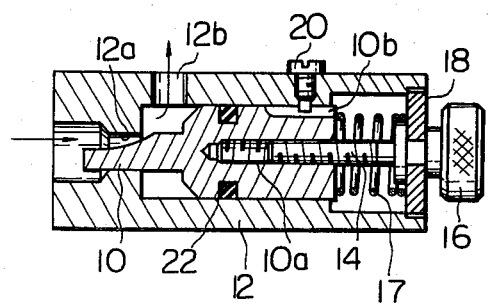
FIG. 3 is a cross sectional view of one example of a flow rate adjustment valve shown in FIG. 2.

FIG. 3 illustrates a preferred example of a flow rate adjustment valve which employs the needle valve 10 described above. Reference numeral 12 denotes a valve body 12 having an orifice or valve opening 12a through which the tip of the needle valve 10 is moved. The needle valve 10 is adapted to be advanced and retracted by a feed screw 14 such that rotation of a flow rate adjustment knob 16 moves the needle valve 10 through the intermediary of a threaded bore 10a of the needle valve 10. A compression spring 17 is inserted between the needle valve 10 and end closure 18 of the valve body 12 in order to provide play or backlash. Fitted into a key groove 10b is a key 20 adapted to lock the needle valve 10 against rotation. Designated at 22 is an O-ring for maintaining an air-tight seal between the needle valve 10 and valve body 12. Thus, a fluid which enters the valve from the left side as indicated by the arrow undergoes flow rate control in the orifice by the needle valve 10 before flowing out of the valve from an outlet opening 12b. Rotating the flow rate adjustment knob 16 causes the feed screw 14 to move the needle valve 10. As described above, the sectional area of the valve opening is proportional to the distance along the axis of the needle valve 10 from the point at which the sectional area of the opening is zero; hence, whenever knob 16 is turned, it is possible to regulate the flow rate in proportion to the angle through which the knob is rotated.

Figure 4:
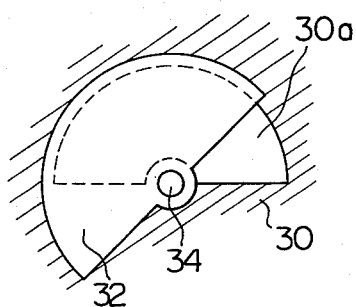
FIG. 4 is a fragmentary cross sectional view of another example of a flow rate adjustment valve which can be incorporated in the anesthesia apparatus according to the present invention.

FIG. 4 illustrates another example of the control valve in which the degree of valve operation can be made proportional to the valve opening area. In this case a valve body 30 has a semi-circular valve opening. Here, a fan-shaped valve 32 is rotatably secured to the valve body 30 by means of a shaft 34. When the fan-shaped valve 32 is rotated from the closed position its angle of rotation is proportional to the effective cross sectional area of the opening 30a.

Figure 5:
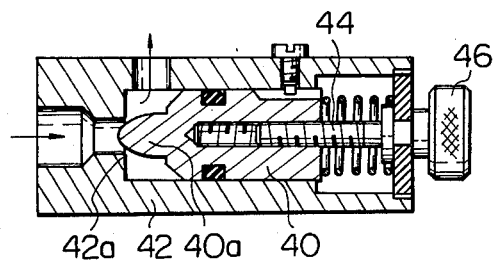
FIG. 5 is a cross sectional view of still another example of a flow rate adjustment valve which can be incorporated in the anesthesia apparatus according to the present invention.

FIG. 5 shows another example of a needle valve 40 having a tip 40a the configuration of which is determined by rotating a parabola about the center line of the valve. This arrangement makes it possible to establish a proportional relation between the amount of needle valve movement and the effective cross sectional area between an orifice 42a of a valve body 42 and the tip of the needle valve 40. Indicated at 44 is a feed screw and 46 a knob connected to the feed screw 44.

Figure 6:
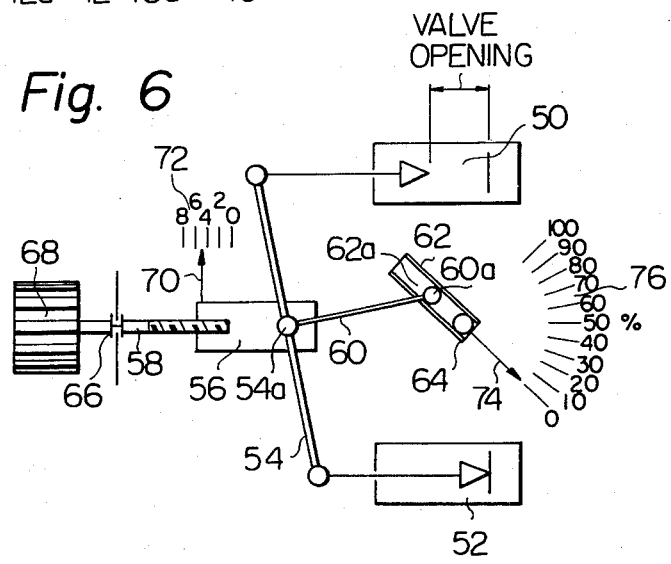
FIG. 6 is a schematic view illustrating a principle of the anesthesia apparatus according to the present invention.

FIG. 6 shows a schematic diagram for illustrating a principle of an anesthesia apparatus according to the present invention. First and second flow rate adjustment valves 50 and 52 are adapted to vary flow rate in proportion to the degree of movement. The first and second flow rate adjustment valves 50 and 52 are connected by a connecting lever 54 pivotal about its center 54a, which is connected to a member 56 engaging a feed screw 58. Connecting lever 54 includes an arm 60 extending from its center, the end 60a of the arm engaging a groove 62a of a compensating cam 62. The groove 62a is pivotal about a compensating cam shaft 64 supported by a frame (not shown). Feed screw 58 is also supported by the frame by means of a bearing 66 such that rotation of an adjustment knob 68 actuates the feed screw 58 which causes member 56 to move axially of the screw. The degree to which member 56 moves is directly related to the opening degree of the valves 50 and 52. For example, if a flow rate indicating needle 70 is attached to a portion of member 56, the total value of the valve openings of the first and second flow rate adjustment valves 50 and 52 can be read off flow rate graduations 72 provided on the frame. Since the opening degree of the adjustment valves is proportional to the flow rate of the fluids passing therethrough, the flow rate indicating needle 70 directly indicates the total flow rate of the fluids passing through both valves 50 and 52 if the graduations 72 are suitably spaced. Similarly, the proportions of the fluidic components flowing through the respective flow rate control valves can be obtained by a mixture ratio indicating needle 74 mounted on the compensating cam shaft 64 and a mixture ratio graduated scale 76 provided on the frame. The value of the opening degree of flow rate adjustment valve 52 with respect to the total value of the opening degree of both flow rate adjustment valves is a percentage of the fluid flowing through valve 52. In a case where the mixture ratio scale 76 is adapted to indicate the ratio (%) of the flow rate on the side of valve 52 to the total flow rate for the arrangement of components illustrated in FIG. 6, the 0 position of the scale is located to the left of the center or 50% position, and the 100% position is symmetrically located with respect to the 0% graduation. When compensating cam groove 62a is inclined by a given angle and member 56 is moved by the feed screw 58, the angle can be chosen such that the movement of cam groove 62a, connecting lever 54 as well as its arm 60 and arm tip 60a causes flow rate adjustment valve 50 to move through twice the distance traveled by member 56, while the other flow rate adjustment valve 52 remains absolutely stationary. At this time, the angle of inclination of cam groove 62a corresponds to a mixture ratio of 0%. In a case where the mixture ratio is 50%, valves 50, 52 open equally when flow rate adjustment knob 68 is rotated. In other words, if the arm tip 60a of connecting lever 54 moves in cam groove 62a without any transverse movement, connecting lever 54 will undergo parallel motion so that the degree to which valves 50, 52 open will increase while their respective opening areas remain equal; hence, the flow rate increases with the mixture ratio maintained at 50%.

The graduations between the 0% and 50% graduations are obtained based upon the opening area values of both valves 50, 52. When the pivot point 54a of connecting lever 54 is shifted by feed screw 58, arm tip or engagement pin 60a slides in cam groove 62a that is inclined at a given angle, and allows the opening degree of valves 50, 52 to be controlled while maintaining constant the mixture ratio decided by the angle of inclination of the cam groove 62a. Accordingly, the mixture ratio remains unaffected regardless of the flow rate. Furthermore, when cam groove 62a is rotated with the total flow rate fixed at a certain value, arm tip 60a located in the groove causes connecting lever 54 to pivot about its center so that the relative proportions of the valve openings can be varied without affecting the total opening area of the valves.

Figure 7:
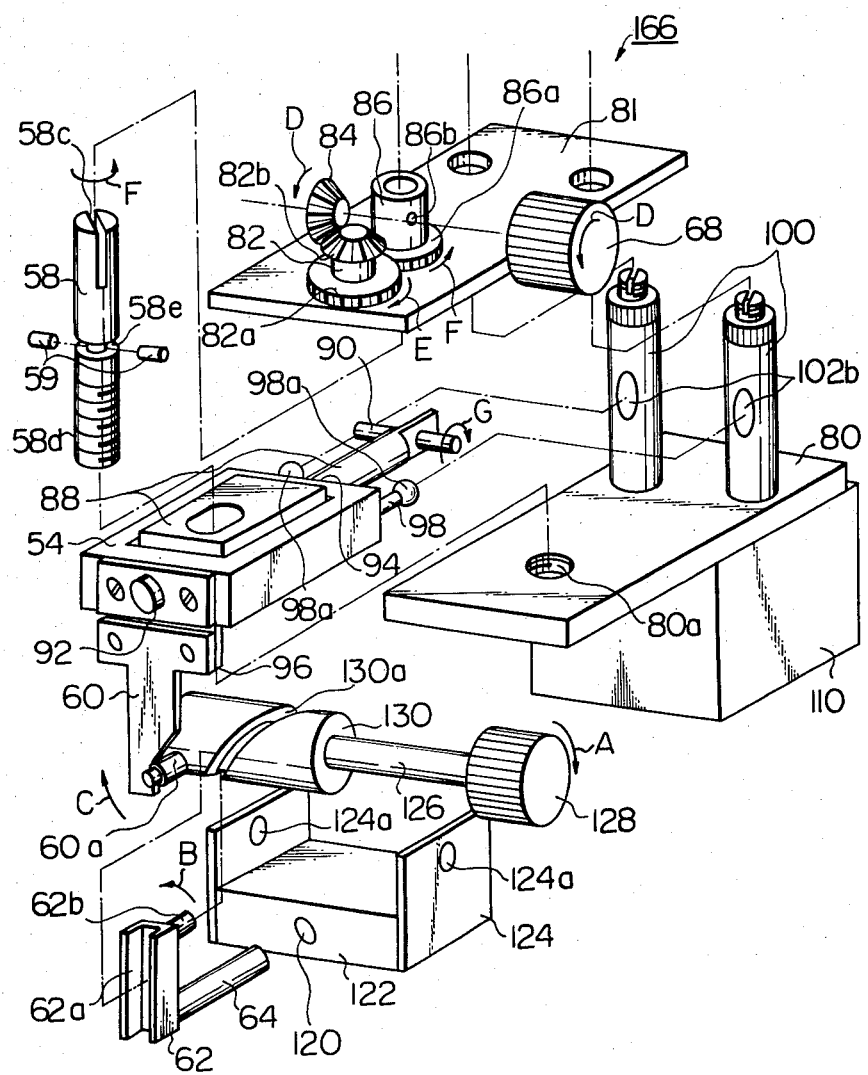
FIG. 7 is an expanded view of a preferred embodiment of a anesthesia apparatus according to the present invention.

FIG. 7 shows a preferred embodiment of the anesthesia apparatus based upon the operational principle of FIG. 6. Reference numerals 80, 81 designate portions of frames of the apparatus. A gear 82 (the shaft of which is not shown) rotatably supported by frame 81 includes a spur gear 82a and bevel gear 82b the latter of which engages with a bevel gear 84 that is rotated by the flow rate adjustment knob 68. This rotation is transmitted from bevel gear 84 to bevel gear 82b, spur gear 82a and finally to a spur gear 86a which engages with gear 82a. Spur gear 86a has a pin 86b in engagement with a slit 58c in the head of feed screw 58 so that rotation of the spur gear 86a is transmitted to the feed screw. Feed screw 58 is supported by a through-hole (not shown) provided in frame 81, and by a threaded bore 80a formed in frame 80, and includes a threaded portion 58d screwed into bore 80a; hence, feed screw 58 undergoes axial movement when rotated. Two pins 59 which engage with an annular recess 58e formed in the shank of feed screw 58 are fixed to a feed lever 88 which is adapted to rock about a feed lever supporting shaft 90 which extends through a hole provided in one end of the lever 88. The feed lever supporting shaft 90 is rotatably supported by the frame. Connecting lever 54 is rotatably supported by bearings 92, 94 connected to feed lever 88. The arm 60 is connected to and vertically extends from one end of the connecting lever 54 by means of a leaf spring 96. The leaf spring 96 is slightly bent to urge the engagement pin 60a of the arm 60 so that the engagement pin 60a is held in engagement with the groove 62a of the compensating cam 62. Connected to the other end of the connecting lever 54 is a pair of actuating shafts 98, each having at its end a ball member 98a. The ball members 98a of the actuating shafts 98 are operatively connected to and actuate flow rate adjustment valves or plungers 100. As best shown in FIG. 8, the plunger 100 comprises a cylindrical body 102 having an axial bore 102a and a transverse bore 102b formed at an upper portion of the cylindrical body 102, a biasing spring 104 disposed in the axial bore 102a, a spring seat 106 slidably received in the axial bore 102a, an adjustment screw 108 to adjust the relative position of the ball member 98a and the plunger 100, and a lock nut 110 screwed onto the adjustment screw 108. The ball member 98a of the actuating shaft 98 extends through the transverse bore 102b and is held in place between the bottom end of the adjustment screw 108 and the upper end of the spring seat 106. A flow rate adjustment valve element 108 having an slanted end 108a is mounted on the bottom end of the plunger 100. The plunger 100 thus arranged is slidably received in an axial bore 110a of a cylinder block 110 secured to the frame 80. The cylinder block 110 also has an inlet 110b formed at the bottom end of the axial bore 110a and supplied with gas under pressure, and an outlet 110c communicating with the axial bore 110a. An orifice or restrictor 112 is provided in the inlet 110b. The flow rate adjustment valve 108 is axially movable through the orifice 112, thereby varying the effective cross sectional area between the orifice 112 and the valve element 108.

Turning now to FIG. 7, the pivot shaft 64 of the compensating cam 62 is rotatably accommodated in a bore 120 formed in a cam support member 122. Support plates 124 are secured to both sides of the cam support member 122 and have bores 124a, respectively, through which a rotatable shaft 126 rotatably extend. The rotatable shaft 126 is connected to and driven by a mixing ratio adjustment knob 128 and carries thereon a cylinder cam 130 having a curved cam recess 130a with which a cam follower pin 62b formed on the compensating cam 62 engages.

With the arrangement mentioned above, the mixing ratio of two gases is determined by rotating the mixing ratio adjustment knob 128. When the knob 128 is rotated, the cylinder cam 130 is rotated together with the rotational shaft 126 connected to the knob 128. In this case, the cam follower pin 60a of the arm 60 of the connecting lever 54 moves along the cam recess 130a so that the compensating cam 62 rotates clockwise or counter-clockwise about the shaft 64 to assume a prescribed angular position. More specifically, if the knob 128 is rotated clockwise as shown by an arrow A in FIG. 7, the compensating cam 62 rotates counter-clockwise as shown by an arrow B, causing the arm 60 and accordingly the connecting lever 54 to rotate clockwise about the axis of the feed lever 88 as shown by an arrow C. Thus, the ball members 98a of the actuating shafts 98 connected to the connecting lever 54 have different levels and the first and second flow rate adjustment valves 100 have different valve openings so that the mixing ratio of the gases is determined to a prescribed ratio. Under this circumstance, if the flow rate adjustment knob 68 is rotated counter-clockwise as indicated by an arrow D, the spur gear 82a rotates clockwise as indicated by an arrow E, rotating the spur gear 86a counter-clockwise as indicated by an arrow F. In this instance, the feed screw 58 rotates counter-clockwise as shown by an arrow F. Since the thread 58d of the feed screw 58 engages with the thread 80a of the frame 80 and the pin 60 of the feed screw 58 engages with the bore formed in the feed lever 88, the counter-clockwise rotating of the feed screw 58 causes upward movement of the feed screw 58. Consequently, the connecting lever 54 is rotated clockwise about the shaft 90 as indicated by an arrow G so that both of the ball members 98a are moved upward whereby the flow rate adjustment valves 100 are moved upward to increase the total gas flow rate without causing any change in the mixing ratio of the gases controlled by the valves 100. In the embodiment shown in FIG. 7, the clockwise rotation of the knob 128 causes clockwise rotation of the connecting lever 54 so that the valve opening of the righthand side flow rate adjustment valve 100 is decreased while the valve opening of the lefthand side flow rate adjustment valve 100 is increased. Similarly, the counter-clockwise rotation of the knob 128 causes the counter-clockwise rotation of the connecting lever 54 so that the valve opening of the righthand side flow rate adjustment valve 100 is increased while the valve opening of the left-hand side flow rate adjustment valve 100 is decreased. In this manner, rotation of the mixing ratio adjustment knob is transmitted through the cylinder cam 130 and the compensating cam 62 to the connecting lever 54 which is consequently rotated about the axis of the feed lever 88, thereby determining the mixing ratio of the gases. Further, counter-clockwise rotation of the flow rate adjustment knob 68 causes clockwise rotation of the connecting lever 54 about the shaft 90 so that the flow rate adjustment valves 100 are moved upward at the same rate. On the contrary, clockwise rotation of the knob 68 causes the counter-clockwise rotation of the connecting lever 54 about the shaft 90 so that the valves 100 are moved downward. In this manner, the total flow rate of the gases is adjusted to a desired value by rotating the knob 68 in a given direction. It will be understood that the mixing ratio can be determined by rotating the mixing ratio adjustment knob 128 in a desired direction for thereby determining the angular position of the compensating cam 62 with respect to the axis of the shaft 64.

In the structure shown in FIG. 7, it is desired that, in order to accurately control the total flow rate, the distance between one end of the connecting lever 54 and the central axis of the shaft 90 be sufficiently greater than the distance between the center of each of the ball members 98a and the central axis of the shaft 90. In order to accurately control the mixing ratio, furthermore, the length of arm 60 of the connecting lever 54 should be sufficiently greater than the value of radius of rotation of the ball member 98a relative to the axis of the feed lever 88. The length of the arm 60 of the connecting lever 54 should also have a value sufficiently greater than the stroke of the arm 60, i.e., three times that of the stroke of the arm 60 by which errors that would otherwise occur when the flow rate of gases is increased can be reduced to a minimum value. A feature of this apparatus resides in that the movement of the flow rate adjustment valve element 108 (see FIG. 8) is effected by the connecting lever 88 in proportion to the movement of the end of the connecting lever 54 (i.e., a portion at which the arm 60 is connected) whereby a large amount of movement (i.e., from 10 to 15 mm of stroke in the vertical direction of the arm 60) of the end of the connecting lever 54 is reflected by a small amount of movement (i.e., from 2 to 3 mm) of the valve element 108 of the flow rate adjustment valve 100. In this case, the lever ratio of the distance between the one end of the connecting lever 54 and the axis of the shaft 90 relative to the distance between the center of the ball member 98a and the axis of the shaft 90 is preferably selected to be 5:1. The ball members 98a are provided on the actuating shafts 98 at symmetric positions relative to the axis of the feed lever 88 and arranged such that the value of the radius of rotation of the ball member 98a about the axis of the feed lever 88 is about seven times that of stroke of the valve element 108 of the flow rate adjustment valve 100 (see FIG. 8) for thereby reducing errors that would otherwise take place when the circular motion of the ball member 98a is converted into a linear motion of the valve 100. The length of the arm 60 of the connecting lever 54 is preferably selected to a value as large as possible, i.e., twice or more the rotational radius of the ball member 98a relative to the axis of the feed lever 88 whereby an accurate movement of the ball member 98a due to the engagement pin 60a engaging the groove 62a of the compensating cam 62 can be maintained.

FIG. 9 shows a front view of the anesthesia apparatus incorporating the mechanism shown in FIG. 7. In FIG. 9, the anesthesia apparatus comprises a first coupling 150 in the form of a nut for connecting an oxygen gas flow pipe 152 to a pipe 154 leading to an oxygen gas pressure regulator 155 valve, and a second coupling 156 in the form of a nut for coupling a nitrous oxide flow pipe 158 to a pipe 160 leading to a nitrous oxide gas pressure regulator 161 flow rate adjustment valve. Indicated as 162 is a base plate on which various components are mounted. The base plate 162 is formed with first and second passageways providing fluid communications between pipe 154 and the oxygen gas pressure regulator and between the pipe 160 and the nitrous oxide gas pressure regulator, respectively, to admit the oxygen gas and the nitrous oxide gas to the respective pressure regulators by which the oxygen gas and the nitrous oxide gas are reduced to prescribed pressure levels, respectively. Since, the adjustment of the flow rates of the gases is performed using flow rate adjustment valves of the same size and structure, the pressure of the nitrous oxide gas whose specific gravity is larger than that of the nitrous oxide gas is reduced to a level which is higher than the oxygen gas at a rate proportional to the specific gravity of the oxygen gas. The oxygen gas thus reduced in pressure is supplied the flow rate adjustment valve for the oxygen gas provided in the cylinder block 110. On the other hand, the nitrous oxide gas is supplied to the flow rate adjustment valve for the nitrous oxide gas provided in the cylinder block 110 through a safety valve (not shown) provided in the cylinder block 110. The safety valve is so arranged as to open the nitrous oxide gas flow circuit only when a primary pressure of the oxygen gas (i.e., a pressure of the oxygen gas supplied from outside, the standard level being 4 kg/cm$^2$) exists. Thus, an accident in which only the nitrous oxide gas is supplied is prevented. Reference numeral 166 designates a flow rate adjustment valve actuating mechanism 166 shown in FIG. 7. As previously noted, the flow rate adjustment valve actuating mechanism 166 includes a flow rate adjustment knob 68 and mixing ratio adjustment knob 128 by which the valve openings of the flow rate adjustment valves 100 are controlled, to adjust the total flow rate of the oxygen gas and the nitrous oxide gas. The respective gases passing through the respective adjustment valves 100 flow into an oxygen gas flow meter 170 an a nitrous oxide gas flow meter 172, respectively, through a supporting member 168 secured to the cylinder block 110. Each of the flow meters 170 and 172 comprises a tapered tube and a float freely movable within the tube. In the illustrated embodiment of FIG. 9, the oxygen gas flow meter 170 is located at right-hand side of the apparatus and the nitrous gas flow meter 172 is located at left-hand side of the flow meter 170. Similarly, the coupling 150 for the oxygen gas flow pipe 152 and the coupling 156 for the nitrous oxide gas flow pipe 158 are located at right-hand side and left-hand side, respectively. The gases passing through the respective flow meters are admitted to a mixing chamber (not shown) provided in a manifold 174 supported by side plates 176 secured to the base plate 162 at their lower ends. The gases are mixed in the mixing chamber and subsequently supplied through an outlet 178 to a patient. Indicated at 180 is an oxygen control lever adapted to be rotatable about a shaft 182. The control lever 180 is rotatable to an OFF or closed position, an ON or open position, and a flash position. At the flash position of the control lever 180, only the oxygen gas may be supplied to the patient in a larger amount when the patient is supplied with an anesthesia gas. At the OFF position, the control lever 180 shuts off the supply of the oxygen gas to the apparatus so that the supply of the nitrous oxide gas is also prevented by the action of the safety valve mentioned above. While it has been a usual practice to shut off the gases by closing the flow rate adjustment valves, it is difficult to completely shut off the supply of the gases because a slight amount of leakage of the gases will take place due to inherent construction of the flow rate adjustment valves. In accordance with the present invention, since the supply of two gases can be shut off by the control lever 180 provided independently of the flow rate adjustment valves 100, any accident due to leakage of the gases through the flow rate adjustment valves can be satisfactorily prevented. Because of such an independent mechanism as a control lever 180, there is no need for closing both of the flow rate adjustment valves 100 when it is desired to stop the supply of the anesthesia gas to the patient. Consequently, once the mixing ratio is determined by adjusting the knob 128, the mixing ratio can be maintained at a preset value and anesthesia gas of a constant mixing ratio can be always supplied to different patients, to provide convenient operation and save time for control. When the control lever 180 is rotated from its ON position to the flash position, the oxygen gas passing through the pipes 152 and 154 is directly passed to the outlet 178 through a circuit (not shown) directly connecting the pipe 154 and the outlet 178. In a case where the dentist treats a patient, the dentist usually sits right side looking from the patient and lets the patient to repose on a bed. In this case, the dentist faces the head of the patient and places the patient at right side of the dentist. The dentist usually operates various equipments by his right hand and, in this case, the anesthesia apparatus is usually placed in front and left side near the head of the patient. As a result, the anesthesia apparatus may be conveniently manipulated by the dentist's left hand. To this end, the knobs 68 and 128 are placed on left side of the flow meters 170 and 172 on a front face of the apparatus, thereby preventing a condition in which the flow meters 170 and 172 are concealed by the dentist's arm.

While the present invention has been shown and described with reference to a particular embodiment by way of example, it should be noted that any other changes or modifications may be made without departing from the scope of the present invention.

What is claimed is:

1. An anesthesia apparatus for providing a mixture of first and second fluids, comprising:
   a mixing chamber for mixing said first and second fluids;
   first and second flow meters communicating with said mixing chamber;
   first means for supplying said first fluid to said mixing chamber through said first flow meter;
   second means for supplying said second fluid to said mixing chamber through said second flow meter;
   first and second flow rate adjustment valve means disposed between said first flow meter and said first means and between said second flow meter and said second means, respectively, each of said first and second flow rate adjustment valve means including orifice means and a valve element movable relative to said orifice means and having a predetermined shape to vary the effective cross sectional area between said orifice means and said valve element substantially linearly in proportion to the amount of movement of said valve element;
   actuating means connected to the valve elements of said flow rate adjustment valve means for actuating said valve elements relative to respective ones of said orifice means;
   compensating means operatively connected to said actuating means and operative to set a selected angular position of said actuating means with respect to said valve elements of said flow rate adjustment valve means for thereby determining the relative proportions of said first and second fluids passing through said first and second flow rate adjustment valves, respectively; and
   feed means for feeding said actuating means towards directions to vary the total rate of flow of said first and second fluids while maintaining said selected angular position to provide the relative proportions of said first and second fluids;
   said actuating means comprising a feed lever, a connecting lever driven by said compensating means to be rotatable about an axis of said feed lever by which said connecting lever assumes said selected angular position, and first and second actuating shafts extending from said connecting lever and having ball members engaging with said flow rate adjustment valve means, respectively;
   said compensating means comprising first cam means, and second cam means actuated by said first cam means to assume a predetermined angular position for guiding said actuating means so as to permit said valve means to move while maintaining said selected angular position.

2. An anesthesia apparatus according to claim 1, in which said first fluid is an oxygen gas and said second fluid is a nitrous oxide gas.

3. An anesthesia apparatus according to claim 2, further comprising an oxygen gas control lever provided on a front face of said apparatus for controlling the flow of said oxygen gas.

4. An anesthesia apparatus according to claim 3, in which said oxygen gas control lever has an OFF position to shut off the supply of said oxygen gas, an ON position to effect the supply of said oxygen gas, and a flash position.

5. An anesthesia apparatus according to claim 1, in which said first and second flow meters are located in a front face of said apparatus at a right hand side thereof.

6. An anesthesia apparatus according to claim 5, further comprising first and second control knobs for actuating said compensating means and said feed means, respectively, said first and second control knobs being placed on the front face of said apparatus at a left side thereof.

7. An anesthesia apparatus according to claim 1, in which said first and second means comprise first and second pipes, and first and second coupling means disposed on a lower portion of said apparatus and connected to said first and second pipes.

8. An anesthesia apparatus comprising:
   at least two flow meters;
   first means for supplying one fluid to one of said flow meters;
   second means for supplying another fluid to another one of said flow meters;
   at least two flow rate adjustment valve means disposed between the one of said flow meters and said first means and between said another one of said flow meters and said second means, respectively, each of said flow rate adjustment valve means including orifice means and a valve element having a predetermined shape to vary the rate of flow of each of said fluids substantially linearly in proportion to the amount of movement of said valve element;
   actuating means connected to the valve elements of said flow rate adjustment valve means for actuating said valve elements relative to respective ones of said orifice means;
   compensating means operatively connected to said actuating means and operative to set a selected angular position of said actuating means with respect to said valve elements of said flow rate adjustment valve means for thereby determining the relative proportions of said fluids; and feed means for feeding said actuating means toward directions to vary the total rate of flow of said fluids while maintaining said selected angular position to maintain said relative proportions of said fluids;

said actuating means comprising a feed lever, a connecting lever driven by said compensating means to be rotatable about an axis of said feed lever by which said connecting lever assumes said selected angular position, and first and second actuating shafts extending from said connecting lever and having ball members engaging with said flow rate adjustment valve means, respectively;

said compensating means comprising first cam means, and second cam means actuated by said first cam means to assume a predetermined angular position for guiding said actuating means so as to permit said valve means to move while maintaining said selected angular position.

9. An anesthesia apparatus according to claim 8, in which said first fluid is an oxygen gas and said second fluid is a nitrous oxide gas.

10. An anesthesia apparatus according to claim 9, further comprising an oxygen gas control lever provided on a front face of said apparatus for controlling the flow of said oxygen gas.

11. An anesthesia apparatus according to claim 10, in which said oxygen gas control lever has an OFF position to shut off the supply of said oxygen gas, an ON position to effect the supply of said oxygen gas, and a flash position.

12. An anesthesia apparatus according to claim 8, in which said first and second flow meters are located in a front face of said apparatus at a right hand side thereof.

13. An anesthesia apparatus according to claim 12, further comprising first and second control knobs for actuating said compensating means and said feed means, respectively, said first and second control knobs being placed on the front face of said apparatus at a left side thereof.

14. An anesthesia apparatus according to claim 8, in which said first and second means comprise first and second pipes, and first and second coupling means disposed on a lower portion of said apparatus and connected to said first and second pipes.

15. An anesthesia apparatus comprising:

at least two flow meters;

first means for supplying one fluid to one of said flow meters;

second means for supplying another fluid to another one of said flow meters;

at least two flow rate adjustment valve means disposed between the one of said flow meters and said first means and between said another one of said flow meters and said second means, respectively, each of said flow rate adjustment valve means including a valve element having a predetermined shape to vary the rate of flow of each of said fluids substantially in proportion to the amount of movement of said valve element;

third means connected to said flow rate adjustment valve means for actuating said valve means; and fourth means operatively connected to said third means and operative to set a selected angular position of said third means with respect to said flow rate adjustment valve means for thereby determining the relative proportions of said fluids;

said third means being operative to move said flow rate adjustment valve means while maintaining said selected angular position for thereby varying the total rate of flow of said fluids substantially without varying the relative proportions thereof;

said third means comprising a feed lever, a connecting lever driven by said fourth means to be rotatable about an axis of said feed lever by which said connecting lever assumes said selected angular position, at least two actuating shafts extending from said connecting lever and having ball members engaging with said flow rate adjustment valve means, respectively, and means for feeding said feed lever and accordingly said connecting lever toward directions to vary the total rate of flow of said fluids.

16. An anesthesia apparatus according to claim 15, further comprising a base plate, and a cylinder block mounted on said base, said cylinder block having first and second inlets communicating with said first and second means, respectively, first and second bore means communicating with said first and second inlets, respectively, first and second outlets communicating with said first and second bore means, respectively, and first and second orifice means disposed in said first and second bore means, respectively, said valve elements being movable through said first and second orifice means, respectively, to vary the effective cross sectional areas of said valve means.

17. An anesthesia apparatus according to claim 15, in which said fourth means comprises first cam means, and second cam means actuated by said first cam means to assume a predetermined angular position for guiding said third means so as to permit said valve means to move while maintaining said selected angular position.

18. An anesthesia apparatus according to claim 15, in which said first fluid is an oxygen gas and said second fluid is a nitrous oxide gas.

19. An anesthesia apparatus according to claim 18, further comprising an oxygen gas control lever provided on a front face of said apparatus for controlling the flow of said oxygen gas.

20. An anesthesia apparatus according to claim 19, in which said oxygen gas control lever has an OFF position to shut off the supply of said oxygen gas, an ON position to effect the supply of said oxygen gas, and a flash position.

21. An anesthesia apparatus according to claim 15, in which said flow meters are located in a front face of said apparatus at a right hand side thereof.

22. An anesthesia apparatus according to claim 21, further comprising first and second control knobs for actuating said third and fourth means, respectively, said first and second control knobs being placed on the front face of said apparatus at a left side thereof.

23. An anesthesia apparatus according to claim 15, in which said first and second means comprise first and second pipes, and first and second coupling means disposed on a lower portion of said apparatus and connected to said first and second pipes.

* * * * *